United States Patent
Fürnstahl et al.

(10) Patent No.: US 12,056,834 B2
(45) Date of Patent: Aug. 6, 2024

(54) METHOD FOR DESIGNING A REGISTRATION INSTRUMENT FOR OSTEOSYNTHESIS AND A SYSTEM COMPRISING THE REGISTRATION INSTRUMENT

(71) Applicants: MEDACTA INTERNATIONAL SA, Castel San Pietro (CH); UNIVERSITÄT ZÜRICH, Zürich (CH)

(72) Inventors: Philipp Fürnstahl, Eglisau (AT); Ladislav Nagy, Kilchberg (CH); Andreas Schweizer, Zumikon (CH)

(73) Assignee: Medacta International SA, Castel San Pietro (CH)

( * ) Notice: Subject to any disclaimer, the term of this patent is extended or adjusted under 35 U.S.C. 154(b) by 1018 days.

(21) Appl. No.: 16/971,644

(22) PCT Filed: Feb. 20, 2019

(86) PCT No.: PCT/IB2019/051380
§ 371 (c)(1),
(2) Date: Aug. 20, 2020

(87) PCT Pub. No.: WO2019/162851
PCT Pub. Date: Aug. 29, 2019

(65) Prior Publication Data
US 2020/0388085 A1 Dec. 10, 2020

(30) Foreign Application Priority Data
Feb. 22, 2018 (EP) .................................. 18158106

(51) Int. Cl.
*A61B 17/17* (2006.01)
*A61B 17/80* (2006.01)
(Continued)

(52) U.S. Cl.
CPC .......... *G06T 19/20* (2013.01); *A61B 17/1728* (2013.01); *A61B 17/808* (2013.01);
(Continued)

(58) Field of Classification Search
CPC ... A61B 17/17; A61B 17/1728; A61B 17/864; G06T 17/00
See application file for complete search history.

(56) References Cited

U.S. PATENT DOCUMENTS

2008/0234763 A1* 9/2008 Patterson ............. A61B 17/863
606/301

FOREIGN PATENT DOCUMENTS

| WO | 2008/138137 A1 | 11/2008 | |
|---|---|---|---|
| WO | WO-2008138137 A1 * | 11/2008 | ......... A61B 17/1703 |
| WO | 2013/156545 A1 | 10/2013 | |

OTHER PUBLICATIONS

International Search Report and Written Opinion issued by the International Searching Authority (ISA/EP) in Application No. PCT/IB2019/051380 on Sep. 11, 2019, 11 pages.
(Continued)

*Primary Examiner* — Si Ming Ku
(74) *Attorney, Agent, or Firm* — Meunier Carlin & Curfman LLC (57) ABSTRACT

The invention relates to a method for designing a patient-specific registration instrument for use in osteotomies and a surgical tool system comprising a registration instrument and an osteosynthesis plate.

13 Claims, 6 Drawing Sheets

(51) Int. Cl.
*A61B 17/84* (2006.01)
*A61B 17/86* (2006.01)
*G06T 17/00* (2006.01)
*G06T 19/20* (2011.01)
*A61B 34/10* (2016.01)

(52) U.S. Cl.
CPC .......... *A61B 17/848* (2013.01); *A61B 17/864* (2013.01); *G06T 17/00* (2013.01); *A61B 2034/102* (2016.02); *A61B 2034/105* (2016.02)

(56) References Cited

OTHER PUBLICATIONS

Schweizer, Andreas, et al. "Computer-Assisted 3-Dimensional Reconstructions of Scaphoid Fractures and Nonunions With and Without the Use of Patient-Specific Guides: Early Clinical Outcomes and Postoperative Assessments of Reconstruction Accuracy." The Journal of Hand Surgery, vol. 41, issue 1 (2016): pp. 59-69.
Vlachopoulos, Lazaros, et al. "Three-Dimensional Corrective Osteotomies of Complex Malunited Humeral Fractures Using Patient-Specific Guides." Journal of Shoulder and Elbow Surgery, vol. 25, issue 12 (Dec. 2016): 2040-2047, Abstract Only.
Extended European Search Report issued by the European Patent Office in Application No. 18158106.7 on Aug. 31, 2018, 10 pages.
Vlachopoulos, Lazaros, et al., "Three-Dimensional Corrective Osteotomies of Complex Malunited Humeral Fractures Using Patient-Specific Guides," Journal of Shoulder and Elbow Surgery, vol. 25, issue 12 (Dec. 2016): 2040-2047. https://doi.org/10.1016/j.jse.2016.04.038.

\* cited by examiner

METHOD FOR DESIGNING A REGISTRATION INSTRUMENT FOR OSTEOSYNTHESIS AND A SYSTEM COMPRISING THE REGISTRATION INSTRUMENT

The invention relates to a method for designing a registration instrument for osteosynthesis as well as to a surgical tool system comprising a registration instrument and an osteosynthesis plate.

Osteosynthesis is a surgical procedure during which the anatomical shape of a fractured bone is restored by repositioning the broken bone fragments and subsequently fixing the repositioned fragments.

Particularly in complex fractures of joints the risk of a malunion of the fragments is high and can have severe consequences to the well-being of the patient.

Inaccurately reduced fragments can lead to pain and arthrosis. While the technical term "reduced" refers to the repositioning of the fragments, the term "reposition" is also used to refer to the reduction of the fragments in the following.

In the state of the art [1] computer-assisted three-dimensional reconstructions of scaphoid nonunions of two fragments with patient-specific guides are known to overcome the problem of malunions at least to some extent. According to [1] the method is performed on pseudo-arthrotic patients.

The method according to [1] teaches the acquisition of a three-dimensional surface model of the malunion and subsequently designing a registration instrument that is used during surgery for registering the bone fragments.

For restoring the bone to its "unbroken" state, a three-dimensional surface model of the unbroken bone is determined (also referred to as reconstruction model) such that a predefined healing position of the fragments can be estimated from this model, into which the fragments should be repositioned during surgery.

The registration instrument comprises guiding channels for drilling pilot holes at predefined positions and predefined orientations in the fragments.

While the registration instrument is still in contact with the fragment, Kirschner-wires (in the following referred to as K-wires) can be inserted in some or all of the pilot holes.

The K-wires are used for repositioning the fragments into the predefined healing position by orienting the K-wires parallel to each other. This is done by moving the fragments in the desired and predefined healing position, particularly with the registration instrument being removed from the fragment during reposition.

According to [1], a post-registration instrument comprising parallel centering channels for the K-wires can be slid on the K-wires with its centering channels. The post-registration instrument is designed for bringing the fragments in the intended exact position with respect to each other.

The post-registration instrument has an additional opening that is configured to guide a compression screw through the fragments and thus to fix the fragments in the predefined position.

A problem in this procedure is that it is difficult to identify the correct position of the registration instrument on the fragment during surgery. The surgeon has to approximate the position of the registration instruments by comparing the position of the registration instrument with the computer model.

Also, this procedure is not suitable when the fragments are completely disjoint and mobile or when more than two fragments need to be repositioned and joined.

While this procedure [1] is suitable for mal- and non-unions it bears many problems for fracture treatment.

One of the reasons for this is that in fractures the fragments can be comparably mobile causing the repositioning being error-prone, time-consuming, and technically difficult.

Even the positioning of the registration instrument is challenging in this situation.

An object of the present invention is to overcome the problems know in the state in the art.

The objective is achieved by a method for designing a patient-specific registration instrument for use in osteotomies and osteosynthesis, comprising the features of claim 1.

Advantageous embodiments are described in the sub-claims.

According to claim 1, the method comprises at least the following steps:

Acquiring a three-dimensional model, particularly a three-dimensional surface model of a fractured bone, wherein the fractured bone is broken in a plurality of fragments, that are at least partially disjoint, particularly each fragment exhibiting a pathological fractured surface, such as a protruding edge fraction;

Determining a first particularly extra-articular surface portion of one fragment, wherein the first surface portion comprises a pathological edge surface, and determining a second surface portion of the fragment, wherein the second surface portion comprises a non-pathological bone surface, particularly wherein the first and second portion meet at an edge;

Designing and particularly manufacturing a registration instrument comprising a first and a second contact surface, wherein the first contact surface is an inverse surface of the first surface portion of the fragment and the second contact surface is an inverse surface of the second surface portion of the fragment, wherein the first and second contact surface are configured such that the registration instrument fits to the fragment, only when the first and second contact surface are aligned with the first and second surface portion of the fragment.

The method according to the invention is particularly well-suited for designing a registration instrument for a fractured scaphoid, a fractured distal radius or a fractured pelvis.

The acquisition of the three-dimensional model of the bone can for example be achieved by analysis of computer-tomography data comprising the fractured bone. Other imaging methods can be used for generating the three-dimensional model of the bone.

The three-dimensional model of the bone is particularly an accurate representation of the fractured bone. The surface of the bone can be modeled with a mesh (surface model) or by an image consisting of suitable polygons or voxels at a suitable resolution. The model can be a virtual computer model.

The three-dimensional model of the bone particularly comprises all fragments or only a selected fragment. The three-dimensional model of the bone can comprise three-dimensional sub-models each comprising a fragment of the bone. These sub-models can be virtually repositioned against each other.

The fractured bone can comprise fragments that are not completely separated from each other, i.e., the fragments are connected in some areas of the bone and disjoint in other areas. However, the fragments might also be completely disjoint.

In a next step, two different surface portions of the fragment are identified particularly with the help of the three-dimensional model, for which the registration instrument is designed. A first surface portion extends in an area that is pathological, i.e., it comprises an area where the bone has been damaged. Such a pathological area particularly is or has not been exposed to the surrounding of the bone prior to the fracture.

The first surface portion particularly comprises or consists of an edge or a portion of an edge of the fragment that extends along the fracture.

The second surface portion is a non-pathological surface portion of the fragment, wherein this portion particularly comprises an area of the fragment that is exposed to the surrounding tissue of the bone when the bone is in its healthy, i.e., unbroken/non-fractured state.

The first and the second surface portion therefore particularly provide an edge along which the first and the second surface portion meet. This edge is particularly the fracture edge.

This edge particularly provides a landmark in terms of positioning the registration instrument.

For this reason, the registration instrument according to the invention comprises the first and the second contact surface that are designed as inverse surfaces to the first and second surface portion of the fragment.

The inverse surface is a complementary surface of the first and second portion. Inverse surfaces are particularly identical but oriented in the opposite direction, i.e., the orientation vectors of the surfaces point in opposite directions. Therefore, inverse surfaces can be aligned with non-inverse surfaces without a gap between them.

The first and/or the second portion can comprise a plurality of sub-portions that are particularly disjoint from each other.

Therefore, when the first contact surface is aligned with the first surface portion of the fragment the fit between the contact surface and the first surface portion is best.

The same applies for the second surface portion and the second contact surface.

When the first and the second contact surface are brought into contact and into alignment with the first and second surface portion of the fragment, the degrees of freedom for moving the registration instrument relative to the fragment are reduced as the registration instrument particularly experiences a slight interlock or lock-in, when the corresponding first and second surfaces align.

In order to allow a fit of the registration instrument only if the contact surfaces are aligned with the corresponding surface portions of the fragment, the surface portions of the fragment and thus the contact surfaces particularly comprise a non-planar surface, i.e., at least the first or the second contact surface (and thus the corresponding surface portions of the fragment) comprise protrusions, cavities or edges that are unique features of the surface.

Alternatively, or additionally, the contact surfaces (and thus the corresponding surface portions) form a two-dimensional manifold that is unique for the fragment such that a unique positon is defined at which the registration instrument fits to the fragment.

For this purpose, the first and second contact surface of the registration instrument can enclose an angle that is smaller than 180°, particularly smaller than 120°.

The registration instrument fits to the fragment particularly when the first and second contact surfaces of the registration instrument are aligned gapless to the surface portions of the fragment. As both, the contact surfaces and the fragment surface, are rigid, the "correct" fit position between the registration instrument and the fragment can be determined.

The surfaces are particularly considered to be aligned when the contact surfaces and the surface portions coincide, i.e., particularly when corresponding surface features, such as protrusions, cavities, and edges of the contact surfaces and the surface portions coincide.

Due to the unique fit position of the registration instrument on the fragment, this best matching position between the fragment and the registration instrument is comparably simple to identify by the surgeon during surgery.

Therefore, a registration instrument comprising the first and the second contact surfaces formed as inverse surfaces to the first and the second surface portion provides a more accurate positioning than the registration instruments in the state of the art.

In some embodiments the registration instrument comprises more contact surfaces than the first and the second contact surface.

The purpose of the registration instrument is particularly to identify predefined pilot hole positions on the fragment such that subsequent surgery steps, e.g. repositioning of the fragments, can be carried out with high precision at the identified positions. The pilot hole positions can be used to reposition the fragment to a predefined healing position that corresponds to a position in which the bone should be reconstructed from the fragments. Therefore, the registration instrument serves to accurately register these predefined positions.

The positons are particularly positions for surgical pins, such as K-wires, surgical screws, and other fixing and orientation means for surgery. The more precise these positions can be estimated, the higher the probability of a full recovery of the bone and the patient will be.

The registration instrument is then manufactured according to the three-dimensional model.

The registration instrument can be tested virtually or in real world on the three-dimensional model in order to simulate the surgery, as the three-dimensional model is an exact replica of the fractured bone, particularly the surface of the fracture bone.

The registration instrument comprises or consists of a sterile compound such as a suitable polymer like Polyamide 12 (CAS Registry Number: 24937-16-4). The registration instrument can particularly be manufactured using an injection moulding process or a rapid prototyping technique, such as 3D-printing.

The method according to the invention is particularly well-suited for osteosynthesis of joints, when the fragments are completely disjoint and separated. In these kinds of fractures, it is particularly difficult for a surgeon to determine the correct position and alignment of the fragments with respect to each other. Also, the fragments in this situation are comparably mobile, which complicates the comparison with prerecorded fracture models and the positioning by conventional registration instruments.

According to another embodiment of the invention, for each fragment comprising a first and a second surface portion, a separate registration instrument is designed and manufactured particularly according to the above laid-out principles.

Each registration instrument can then be either subsequently or simultaneously applied to the fragments and on each fragment predefined positions for repositioning the fragment with the use of positioning and orientation aids, such as K-wires can be identified.

Each registration instrument is a patient-specific instrument that has to be manufactured individually for each fracture.

According to another embodiment of the invention, the first and the second surface portion of the fragment are determined such that they are accessible to the registration instrument during surgery, particularly along a predefined trajectory, and that the first and the second surface portion of the fragment form a constraint for a further motion of the registration instrument, particularly beyond the trajectory and along a motion transverse to the predefined trajectory of the registration instrument, when the registration instrument is in contact and aligned to the first and the second surface portion with its corresponding first and second contact surfaces.

The areas comprising the first surface portion and the second surface portion of the fragment are particularly determined by the following factors.

The first surface portion and the second surface portion have to be accessible during surgery.

The term "accessible" in this context refers to the surgically exposed fragment surfaces. Which portions are exposed is decided by the surgeon. Following this decision, the first and second surfaces can be identified.

Other components that are used in subsequent steps as repositioning aids, such as surgical pins, like K-wires, might pose constraints for application and removal of the registration instrument on/from the first surface and second surface.

Considering this embodiment, a trajectory for the application and removal of the registration instrument is determined under which the registration instrument can be approached and removed to the first and second surface portions of the fragment.

The first and the second surface portion provide a constraint to motions particularly beyond the determined trajectory and also laterally to the determined trajectory when the registration instrument is aligned and in contact with the first and second surface portion.

This constraint can be recognized and identified by the surgeon when placing the registration instrument at the correct position on the fragment during surgery.

As the first and second surface portions particularly meet at an edge or form an edge, which can serve as the constrain where the registration instrument can be brought to a stop, when the corresponding surfaces of the registration instrument and the fragment are aligned and in contact.

When the registration instrument is in contact and aligned with the fragment, the degrees of freedom for moving the registration instrument are reduced to such an extent that the registration instrument can be moved particularly only backwards or in a backwards direction along the predefined application trajectory, as long as the applied forces are within reasonable range.

According to another embodiment of the invention, a plurality of straight guiding channels at predefined positions and in predefined orientations in the registration instrument are determined and manufactured into the registration instrument, wherein each guiding channel is configured to provide guidance for a surgical tool to a predefined position and in a predefined orientation for a pilot hole in the bone surface, particularly in the fragment.

Such surgical tool can be a surgical drill for drilling the pilot hole at the predefined position and in the predefined orientation into the bone or a surgical pin that is to be inserted into the pilot hole in the predefined orientation.

For drilling additional drill sleeves can be inserted in the guiding channels.

Each pilot hole particularly comprises a pilot hole axis along which the pilot hole extends.

The orientation of the guiding channel of the aligned registration instrument and the corresponding pilot hole axis are identical.

Some of the guiding channels can be configured to receive and guide a surgical pin into a drilled pilot hole at the predefined position and orientation.

The surgical pins particularly serve to achieve and determine the predefined position of the fragment for healing in subsequent steps.

A surgical pin can be a K-wire, a straight or rigid pin, a bar-like device, wherein the surgical pin is configured to be inserted in the pilot hole.

The surgical pin consists particularly of a biocompatible stainless steel. The surgical pin has particularly a cylindrical outer shape.

For each fragment that is to be aligned with the aid of the registration instrument, at least one guiding channel is arranged accordingly on the registration instrument. If possible, it is preferred to provide two or more guiding channels per fragment on the registration instrument. However, if the fragment size is too small, a single guiding channel can be used as well for the fragment.

The registration instrument is configured to identify predefined positions on the bone, particularly on the fragment and to drill pilot holes at these predefined positions and along the predefined orientations, wherein the pilot holes are oriented along a predefined axis, such that surgical instruments, such as surgical pins, K-wires, plate components, or screws can be inserted along the predefined orientation into the pilot hole.

According to another embodiment of the invention, at least some of the guiding channels are arranged in such a way on the registration instrument that the predefined positions for pilot holes are on a different fragment of the fractured bone. This for example allows for a registration instrument that is designed such that once it is aligned to the fragment with its contact surfaces, the registration instrument extends to a second fragment, wherein at least some guiding channels of the registration instrument are configured to provide guidance for drilling pilot holes into this second fragment.

This embodiment is suitable when the fragments are not completely disjoint or when both fragments can be aligned with a single registration instrument. Then, a single registration instrument can be used to identify the predefined positons for the pilot holes on separate fragments, which provides an efficient process for identifying the pilot holes.

According to another embodiment of the invention, two or at least one guiding channels are arranged such on the registration instrument that the predefined positions for pilot holes are on the same fragment of the fractured bone that comprises the first and second surface portion for the registration instrument.

According to another embodiment of the invention, at least some of the guiding channels are arranged such on the registration instrument that the predefined positions for pilot holes are on the fragment comprising the first and second surface portion.

This embodiment is suitable, when the fragments are disjoint and particularly comparably mobile. In these cases the relation between the fragments is not fixed and the registration of fragments would be imperfect when using only a single registration instrument for registering a plurality of fragments.

According to another embodiment of the invention, at least one guiding channel for receiving a surgical pin, such as a K-wire, comprises a slit in the channel wall along the axis of said channel, wherein the slit has a greater diameter than the surgical pin such that the registration instrument can be radially removed by releasing a surgical pin inserted in said guiding channel through the slit rather than through the channel openings.

This embodiment allows for a greater flexibility of removing the registration instruments from the fragment after surgical pins are inserted. The surgical pins can lead to a reduction of degrees of freedom to remove the registration instrument. By a guiding channel that comprises a slit, this reduction can be at least partially prevented.

According to another embodiment of the invention, a three-dimensional reconstruction model, particularly a three-dimensional reconstruction surface model is generated that represents the surface of an unfractured bone configuration of the fractured bone, wherein the reconstruction model comprises the repositioned fragments and particularly the correspondingly repositioned orientations and positions of the pilot holes or other landmarks in the fragments and particularly the repositioned surgical wires, surgical pins, and surgical screws attached to the fragments.

The reconstruction model particularly comprises also a model of an osteosynthesis plate and its position relative to the repositioned fragments that is used for fixing the fragments to their intended positions during surgery.

Various embodiments of the osteosynthesis plate are elaborated in the following.

There are different methods of determining such a reconstruction model, for example by using data acquired from the bone prior to the injury, or by using data from a contralateral bone or by using statistical methods for reassembling the fragments virtually, or by assembling the fragments virtually in a manual fashion.

In the reconstruction model the fragments are joined such that particularly the pathological first surface portion is not exposed anymore to the surrounding tissue. It might be that some minor surface portions of the first surface are still exposed to the surrounding tissue after the fragments are joined, in case bone splinters or marginal bone fragments are present in the fractured bone that are too small to be repositioned. These splinters should thus be removed during surgery.

The pilot holes and thus the guiding channels on the registration instrument can be arranged such that the pilot holes and particularly the pilot holes comprising surgical pins of different fragments are oriented parallel to each other after repositioning according to the reconstruction model. This allows a comparably simple estimation of the correct alignment of the pilot holes, the surgical pins and thus of the fragments.

According to another embodiment of the invention, the reconstruction model comprises the repositioned fragments and the corresponding orientations and positions of pilot holes in the fragments, wherein an osteosynthesis plate is designed, particularly designed and manufactured, particularly by using the reconstruction model. The osteosynthesis plate comprises a plurality of openings that correspond to the positions and orientations of the pilot holes after repositioning the fragments.

In some embodiments at least some of the openings in the osteosynthesis plate comprise a thread, wherein a thread axis of the thread is oriented along a corresponding pilot hole axis of the repositioned fragment.

According to another embodiment of the invention, at least some of the openings in the osteosynthesis plate comprise a thread, wherein a thread axis of the thread is oriented along a corresponding pilot hole axis of the repositioned fragment.

The osteosynthesis plate can be manufactured patient-specific, i.e., shaped according to the specific fracture, or it can be provided in a standardized shape that is applicable to a wide variety of fractures.

The osteosynthesis plate can be used to achieve a more accurate repositioning of the fragments as compared for example in surgeries where no osteosynthesis plate is used but for example only fixation screws and/or surgical pins.

The osteosynthesis plate is particularly manufactured from a surgical material that is suited for implants. The osteosynthesis plate is particularly manufactured from metal (titanium or stainless steel).

The openings in the osteosynthesis plate are arranged such that they provide an orientation for a surgical tool, such as surgical screws for fixing the osteosynthesis plate to the fragment. The orientation can be provided in terms of a thread that extends along a predefined thread axis of the opening such that the surgical tool can be inserted only along this direction.

The osteosynthesis plate is configured to rigidly connect the fragments in the predefined position such that the fragments particularly are arranged as determined in the reconstruction model.

The connection of the osteosynthesis plate with the fragments is particularly achieved by surgical screws for implants, wherein the screws are particularly uniaxial.

However, it is also possible to use multiaxial screws that can be inserted at various angles in the fragment. As the pilot hole already defines a direction even the multiaxial screws can be inserted in the specific orientation.

In some case the screws can be also conventional compression screws.

According to another embodiment of the invention, the osteosynthesis plate comprises pins screwed in the threads and wherein the pins are configured to be inserted in the pilot holes.

This embodiment allows for a facile repositioning and stabilization of fragments with the osteosynthesis plate.

According to another embodiment of the invention, a separate registration instrument is designed and manufactured for each fragment.

Each registration instrument is then configured to register some pilot holes for repositioning the corresponding fragment.

The fragments together with the pilot holes are repositioned during surgery such that they end up on the predefined position according to the reconstruction model.

According to another embodiment of the invention, each registration instrument comprises a connection portion that is formed such that it can be connected via the connection portion to another connection portion of another registration instrument of the plurality of registration instruments.

This embodiment allows the registration instruments to be used also for repositioning of the fragments.

When all pilot holes are drilled in the fragments and all surgical pins are attached to the fragments, the plurality of registration instruments can be connected via the connection portion to form a single piece, while the connection portion of the registration instruments is formed such that the registration instruments can only be connected in a predefined position and orientation, such that the fragments are repositioned to the predefined position.

The problem according to the invention is furthermore solved by a surgical tool system for osteosynthesis of a fractured bone comprising bone fragments. The surgical tool system comprises navigation aids and a registration instrument for supporting the surgeon to precisely perform a osteosynthesis surgery.

The surgical tool system according to the invention comprises a registration instrument for registering a bone fragment, the registration instrument comprising:
- a first and a second rigid contact surface, wherein the first and second contact portion meet along an edge, particularly at an angle smaller than 180°, particularly at an angle smaller than 120°, particularly wherein the first contact surface is an inverse surface of a first surface portion of the bone fragment of the fractured bone and the second contact surface is an inverse surface of a second surface portion of the fragment, wherein the first surface portion of the fragment comprises a pathological surface and the second surface portion of the bone fragment comprises a non-pathological bone surface, particularly wherein the first and second contact surface are configured such that the registration instrument fits to the fragment only when the first and second contact surface are aligned with the first and second surface portion of the fragment, particularly wherein the edge of the first and second contact surface is configured such that the registration instrument is brought to the stop, when the first surface portion of the fragment and the first contact surface as well as the second surface portion of the corresponding fragment and the second contact surface are in contact and aligned;
- at least two guiding channels configured to provide guidance to a surgical tool such as a drill for drilling pilot holes at predefined orientations and positions into the bone and particularly for receiving a surgical pin;

wherein the system further comprises an osteosynthesis plate for rigidly fixing the fragments together in a predefined position, particularly determined by the reconstruction model and particularly wherein the osteosynthesis plate is configured for being implanted, the osteosynthesis plate comprising a plurality of openings for receiving surgical tools, wherein the openings correspond to the positions and orientations of the pilot holes of the fragments, when the fragments are repositioned in the predefined position, and the osteosynthesis plate is aligned with the repositioned fragments.

The registration instrument can be manufactured according to the principles of the method according to the invention.

Therefore, the registration instrument of the tool system has particularly the same features as the registration instrument according to the method.

The registration instrument particularly comprises the first and the second contact surface, wherein the first contact surface is an inverse surface of the first surface portion of the fragment and the second contact surface is an inverse surface of the second surface portion of the fragment, wherein the first and the second surface portion of the fragment form a constraint for a further particularly translational or rotational motion of the registration instrument beyond a predefined trajectory and along a motion transverse or lateral to the predefined trajectory of the registration instrument, when the registration instrument is in contact and aligned to the first and the second surface portion with the corresponding first and second contact surfaces.

The definitions in the specification given for the registration instrument manufactured according to the method particularly apply for the registration instrument of the system.

The surgical tool system comprises at least one registration instrument. The registration instrument is therefore considered a tool of the tool system.

The registration instrument comprises the first and the second contact surface that are particularly complementary surfaces to the first and second surface portion of the fragment.

The first and the second contact surface meet at an edge, wherein the first and the second contact surface particularly enclose an angle smaller than 180°.

This edge in combination with the first and the second contact surface can be used to identify the exact position of the registration instrument on the fragment during surgery.

The edge particularly provides a constraint to a motion of the registration instrument beyond a predefined trajectory for approaching the fragment with the registration instrument. Furthermore, once the registration instrument is in contact and aligned with its first and second contact surfaces to the first and second surface portion of the fragment, not only a motion beyond the predefined trajectory, but also a motion transversal to the trajectory, particularly along the edge formed by the first and second contact surface is constrained, particularly by the match of the corresponding surfaces.

The constraint particularly manifests itself in such a way that, when the registration instrument is aligned correctly and in contact with the fragment, a transversal force applied to the registration instrument, combined with a slight contact-maintaining force along the predefined trajectory, is not resulting in a transversal movement of the registration instrument, particularly because a slight lock-in of the registration instruments first and second contact surfaces with the corresponding fragment surface provide a motion constraint along the transversal direction.

When aligned correctly at the constraint, neither a transversal nor a motion along the trajectory is possible without displacing the fragment relative to the registration instrument. Some rotational motions are also constrained by the constraint.

The guiding channels of the registration instruments are particularly straight channels that are configured for drilling pilot holes into the bone at predefined positions and orientations. For each fragment that is to be aligned with the aid of the registration instrument at least one guiding channel is provided and arranged accordingly on the registration instrument. Preferentially, two or more guiding channels per fragment are provided on the registration instrument. However, if the fragment size becomes too small, a single guiding channel can be used as well for the fragment.

The registration instrument particularly comprises guiding channels that are configured to receive surgical pins, such as K-wires. The channels that are configured to receive surgical pins are particularly oriented parallel to each other, particularly pairwise parallel to each other.

Alternatively, the guiding channels for receiving surgical pins are not oriented parallel. Then the surgical pins can be temporally removed for removing the registration instrument.

Some guiding channels can comprise a drill sleeve. In order to remove the registration instrument from the fragment the drill sleeve can comprise a vertical slit. The same holds true for the guiding channel.

This way it is granted that once the surgical pins are attached to the fragment the registration instrument can be removed from the fragment by sliding the registration instrument along the direction of the surgical pins.

The registration instrument can extend also to other fragments of the fractured bone and it can also comprise guiding channels for drilling pilot holes into the other fragments.

This is particularly useful when the fractured fragments are not completely disjoint.

The guiding channels can be configured to receive a drill sleeve. Alternatively or additionally, at least one guiding channel can comprise a drill sleeve.

The osteosynthesis plate is configured for being implanted, particularly temporally until the fractured has completely healed, or forever. The implantation requires that the material of the osteosynthesis plate consists of a biocompatible surgical material such as titanium or stainless steel.

The osteosynthesis plate comprises a plurality of openings for receiving surgical tools and for fixing the osteosynthesis plate to the fragments, wherein the openings correspond to the positions and orientations of the pilot holes of the fragments, when the fragments are repositioned in the predefined position.

The openings in the osteosynthesis plate are determined such that the fragments can only be fixed to the osteosynthesis plate, when the fragments with the pilot holes are in the predefined position according to the reconstruction model.

The osteosynthesis plate particularly improves the fixation of a plurality of fragments that are particularly completely separated from each other.

In fractures where the fragments are mobile, an indirect repositioning method is error-prone, time-consuming and technically challenging, as the pilot holes in the mobile fragments not only have to match with to the openings in the osteosynthesis plate, but also during fixation of the osteosynthesis plate they have to be kept at the correct position.

The indirect repositioning method is for example described in [2] in the chapter "reduction guides". Indirect repositioning is referred to as "indirect reduction via pre-drilled screw holes".

While the direct repositioning can be achieved with an additional alignment tool as described further down, the osteosynthesis plate particularly comprises openings that are formed such that they provide a direction to a fixing means or a fixing device, such as a surgical, uniaxial screw for fixing the osteosynthesis plate to the fragments.

Therefore, the osteosynthesis plate provides an additional aid for arranging and keeping the fragments in the predefined positions, once they are aligned.

The predefined position of the fragments can be determined by the reconstruction model as disclosed in this specification.

According to another embodiment of the invention, the surgical tool system comprises a plurality of osteosynthesis screws. The screw can have a predefined length, wherein the length can be determined from the fragment size.

According to another embodiment, at least one guiding channel comprises a slit in a channel wall enclosing the channel, wherein the slit extends along the channel axis such that a surgical pin, such as a K-wire inserted in the guiding channel can be radially removed through the slit and particularly not by moving the registration instrument along the channel axis.

This embodiment allows that guiding channels for receiving surgical pins do not have to be arranged parallel to each other but can be arranged along different orientations.

The removal of the registration instrument can then nonetheless be achieved, while the (non-parallel) surgical pins are attached to the fragment by moving the registration instrument such that the corresponding surgical pin is released through the slit of the guiding channel.

The slit provides an additional degree of freedom once the surgical pins are attached to the fragment.

According to another embodiment of the invention, the system comprises at least one drill sleeve, wherein the drill sleeve is either comprised by the guiding channel or wherein the drill sleeve is configured to be inserted in the guiding channel.

Also the drill sleeve can have a slit extending vertically along the drill sleeve for releasing the registration instrument from non-parallel surgical pins.

According to another embodiment of the invention, the system comprises a plurality of registration instruments, each registration instrument being configured to be aligned with the respective first and second surface portions of one fragment of the plurality of fragments, wherein the system particularly comprises two or three registration instruments, particularly for different fragments of the fractured bone.

According to this embodiment, each registration instrument is configured to register pilot holes for repositioning the corresponding fragment.

The fragments together with the pilot holes are then repositioned during surgery such that they end up in the predefined position according to the reconstruction model.

According to another embodiment of the invention, each registration instrument of the plurality of registration instruments comprises a connection portion that is formed such that it can be connected via the connection portion to another connection portion of another registration instrument of the plurality of registration instruments.

This embodiment allows the registration instruments to be used also for repositioning of the fragments.

When all pilot holes are drilled in the fragments and all surgical pins are attached to the fragments, the plurality of registration instruments can be rigidly connected via the connection portion to form a single rigid piece, while the connection portion of the registration instruments is formed such that the registration instruments can only be connected in a predefined position and orientation, such that the fragments are repositioned to the predefined position.

According to another embodiment of the invention, at least some of the guiding channels are arranged such on the registration instrument that the predefined positions for pilot holes are on a different fragment of the fractured bone.

This embodiment is suitable, when the fragments are not completely disjoint. Then, a single registration instrument can be used to identify the predefined positions for the pilot holes on separate fragments, which provides an efficient process for identifying the pilot holes.

According to another embodiment of the invention, at least one guiding channel is arranged such on the registration instrument that the predefined position for a pilot hole is on the same fragment of the fractured bone that comprises the first and second surface portion for the registration instrument.

According to another embodiment of the invention, at least some of the guiding channels are arranged such on the registration instrument that the predefined positions for the pilot holes are on the fragment comprising the first and second surface portion.

This embodiment is suitable when the fragments are disjoint and particularly comparably mobile. In these cases, the relation between the fragments is not fixed and the registration of fragments would be imperfect when using only a single registration instrument for registering a plurality of fragments.

According to another embodiment of the invention, the system comprises a post-registration instrument, wherein the post-registration instrument is configured to align the fragments of the fractured bone with the osteosynthesis plate, while the osteosynthesis plate is arranged at the fragments, wherein the post-registration instrument is configured to align the positions of the pilot holes with the centers of the openings of the osteosynthesis plate.

The alignment of the osteosynthesis plate with the fragments and in particular with the pilot holes in the fragments might be achieved to a certain degree for example by inserting the surgical pins into corresponding openings in the osteosynthesis plate. However, the openings in the osteosynthesis plate might have a greater diameter than the surgical pins and thus allow an alignment tolerance.

For this reason the post-registration instrument is configured to reduce the amount of such an alignment tolerance of the osteosynthesis plate with respect to the fragments.

The post-registration instrument is particularly designed to align the central axes of the pilot holes with the centers of the corresponding openings of the osteosynthesis plate.

Once this is achieved, the osteosynthesis plate can be fixed to the fragments, e.g., by surgical screws.

According to another embodiment of the invention, the post-registration instrument comprises centering channels for receiving surgical pins, such as K-wires, attached to different fragments of the plurality of fragments, particularly wherein the centering channels of the post-registration instrument are arranged particularly such on the post-registration instrument that surgical pins only fit in the centering channels, when the fragments are repositioned at or in the vicinity of the predefined healing position according to the reconstruction model, wherein the centering channels on the post-registration instrument are particularly oriented parallel to each other.

The post-registration instrument can be placed on the almost repositioned fragments and provides a support for keeping the surgical pins extending from the fragments parallel particularly perfectly parallel to each other. The centering channels of the post-registration instrument are configured to center the surgical pin with respect to the opening of the osteosynthesis plate.

While the post-registration instrument is in place, an osteotomy plate can be fixed to the fragments. After the fragments are fixed to each other the post-registration instrument can be removed.

According to another embodiment of the invention, at least a fraction of the openings of the osteosynthesis plate comprises a thread with an oriented thread axis for a surgical tool, particularly wherein the thread axis of the thread is oriented along a corresponding pilot hole axis of a pilot hole, when the osteosynthesis plate is arranged on the repositioned fragments in the predefined position according to the reconstruction model.

The oriented threads allow for a precise insertion of surgical screws along the predefined orientation into the pilot holes and also for the insertion of other surgical tools such as alignment tools and pins.

Such an alignment tool is disclosed in the next embodiment.

According to another embodiment of the invention, the system comprises an alignment tool, wherein the alignment tool comprises a thread fitting to the thread of the opening of the osteosynthesis plate such that the alignment tool can be rigidly screwed into one opening of the osteosynthesis plate such that is assumes a predefined angle with the osteosynthesis plate and thus particularly with the pilot hole, the fragment surface and particularly with the surgical pins such that the fragments are at the predefined position, when they are being fixed to the osteosynthesis plate.

This alignment tool can be a straight pin for insertion in a corresponding pilot hole. The pin is therefore suitable for fixing a fragment in the predefined position and orientation relative to the osteosynthesis plate. The pin particularly extends along the thread axis of the osteosynthesis plate opening.

An osteosynthesis plate equipped with such a pin can be unequivocally attached to the fragments by inserting the pins in the corresponding pilot holes.

As the openings of the osteosynthesis plate are particularly of greater diameter than the surgical pins, surgical pins extending through an opening of the osteosynthesis plate still have radial play and thus the repositioning can still be slightly off as compared to the reconstruction model.

For this reason, the alignment tool can be configured to reduce the amount of radial play for the surgical pin or any other alignment aid.

According to another embodiment of the invention, the alignment tool comprises a straight channel extending along the thread axis of the alignment tool and thus the opening when the alignment tool is screwed into the opening of the osteosynthesis plate, wherein the straight channel is formed such that it can center a surgical pin and reduce or prevent the radial play of the surgical pin with respect to the opening of the osteosynthesis plate.

By sliding such an alignment tool over the surgical pin, the radial play of the surgical pin in the osteosynthesis plate opening can be reduced to a great extent, i.e., the surgical pin is centered in the opening. The alignment tool therefore is configured to adjust the fragments and the osteosynthesis plate precisely to the predefined positon.

Once the alignment tool is attached to the osteosynthesis plate over the surgical pin, fixing-screws can be screwed into the bone through other openings of the osteosynthesis plate that are now arranged perfectly central with the corresponding pilot hole due to the use of the alignment tool. It is particularly possible to drill the pilot holes for some openings after the alignment tool has brought the fragments and the osteosynthesis plate in alignment and fix the fragments with the fixing-screws.

The alignment tool, when screwed on the osteosynthesis plate is particularly extending away from the bone surface.

According to another embodiment of the invention, the alignment tool is a straight and rigid pin that can be screwed in the thread of an opening of the osteosynthesis plate, particularly with a thread of the straight pin, wherein the pin, when screwed in the opening, extends along the thread axis of the opening and wherein the pin fits in a pilot hole, such that the osteosynthesis plate and particularly the screws that can be screwed in free openings assume a predefined orientation and position with respect to the fragments.

The use of pins for aligning the osteosynthesis plate with the fragments has been described already above. Once the osteosynthesis plate is aligned with the fragments, fixing screws can be inserted in the other openings for fixing the osteosynthesis plate to the bone.

When the osteosynthesis plate is attached to the fragments, the pins of the osteosynthesis plate can be replaced by surgical screws as well.

The pins are particularly made of surgical steel such as titanium or stainless steel. The pins are particularly from the same material as the osteosynthesis plate.

The system particularly comprises a straight and rigid pin that can be screwed in the thread of an opening of the osteosynthesis plate, wherein the pin, when screwed in the opening, extends along the thread axis of the opening and wherein the pin fits in a pilot hole, such that the osteosynthesis plate assumes a predefined orientation and position with respect to the fragments.

According to another embodiment of the invention, the system comprises a cannulated screw that can be screwed in the thread of an opening of the osteosynthesis plate, wherein the cannulated screw is configured to receive a surgical pin such as a K-wire in its cannula and wherein the screw is configured to be screwed further into the pilot hole and rigidly connect the osteosynthesis plate with the bone fragment.

The cannulated screw provides a combined alignment tool and a fixing means for the osteosynthesis plate.

The cannulated screw is particularly configured to fit, center and orient a surgical pin with respect to the corresponding opening through which the surgical pin extends.

While the radial play of the surgical pin in the cannula of the screw is reduced to a great extent, it is possible to simultaneously screw the cannulated screw further into the bone such that the screw fixes the osteosynthesis plate to the bone.

The cannulated screw comprises a thread that corresponds to the thread of the osteosynthesis plate opening and that is configured to be screwed into the corresponding pilot hole.

The surgical pin can be removed once the cannulated screw is inserted in the pilot hole.

This embodiment allows for an osteosynthesis plate with only few openings, which in turn is advantageous when the fragment is comparably small.

In the following, the invention is detailed in terms of exemplary embodiments and figure descriptions. Note that the figures are not to scale.

It is shown in

FIGURE DESCRIPTION

Figure 1:
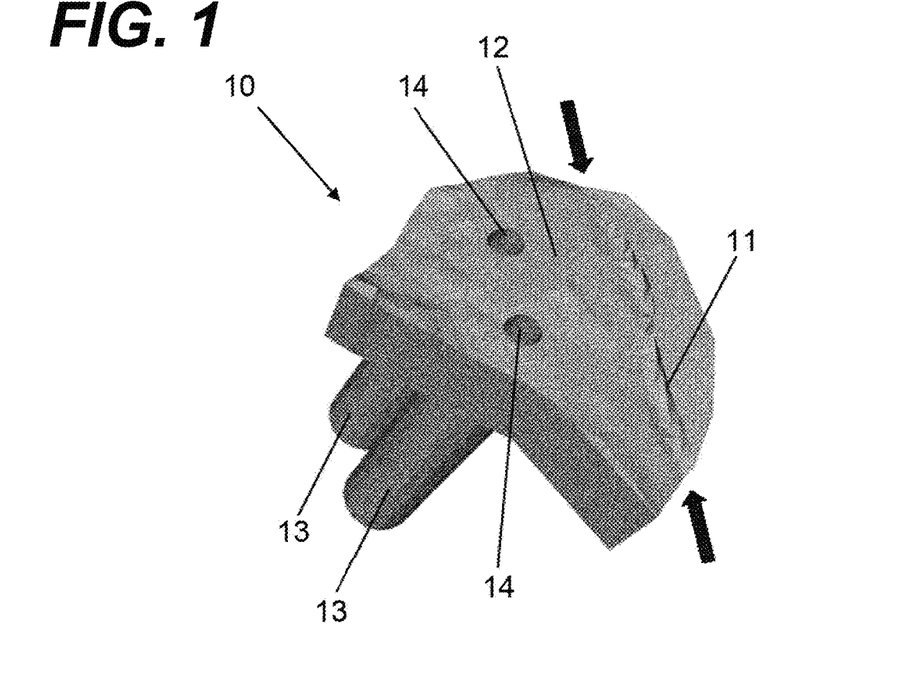
FIG. 1 a three-dimensional view of a registration instrument according to the invention.
Figure 11:
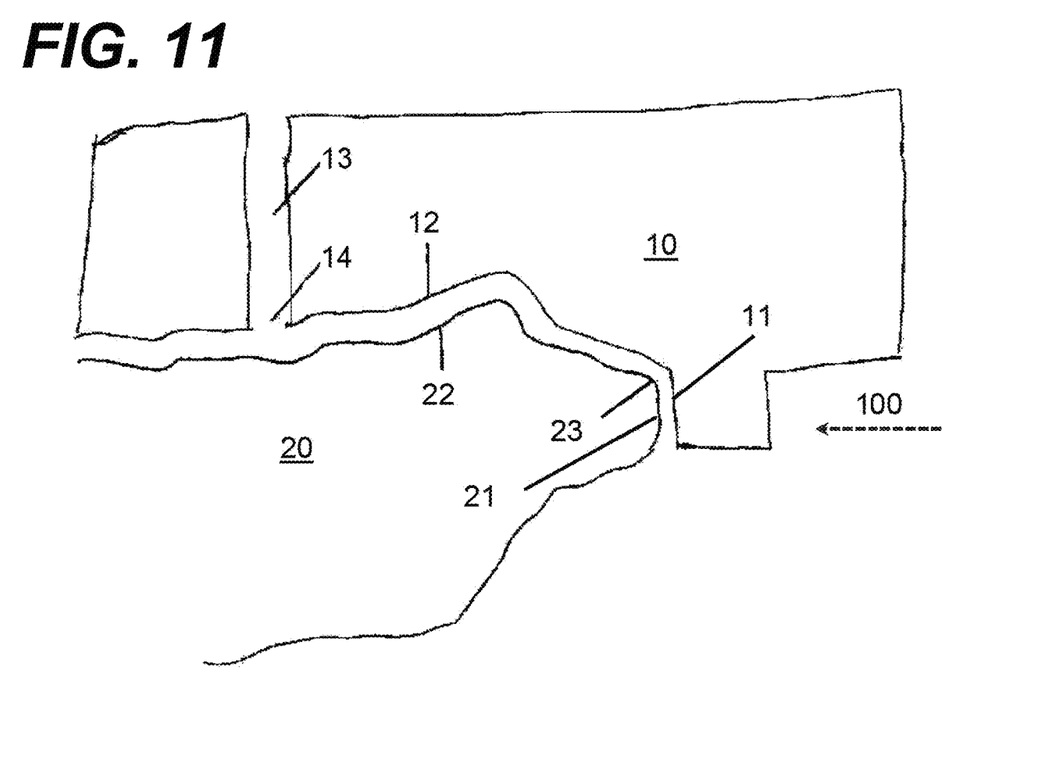
FIG. 11 a cross-sectional view through an registration instrument.

In FIG. 1 a three-dimensional bottom view of a registration instrument 10 is shown and in FIG. 11 a cross-sectional view of the registration instrument 10 aligned to a fragment 20 is shown. The registration instrument 10 comprises a first contact surface 11 and a second contact surface 12 as well as two straight guiding channels 13 that extend parallel to each other and end in two openings 14 on the second contact surface 12. In this example, the guiding channels 13 are essentially orthogonal to the second contact surface 12.

Figure 2:
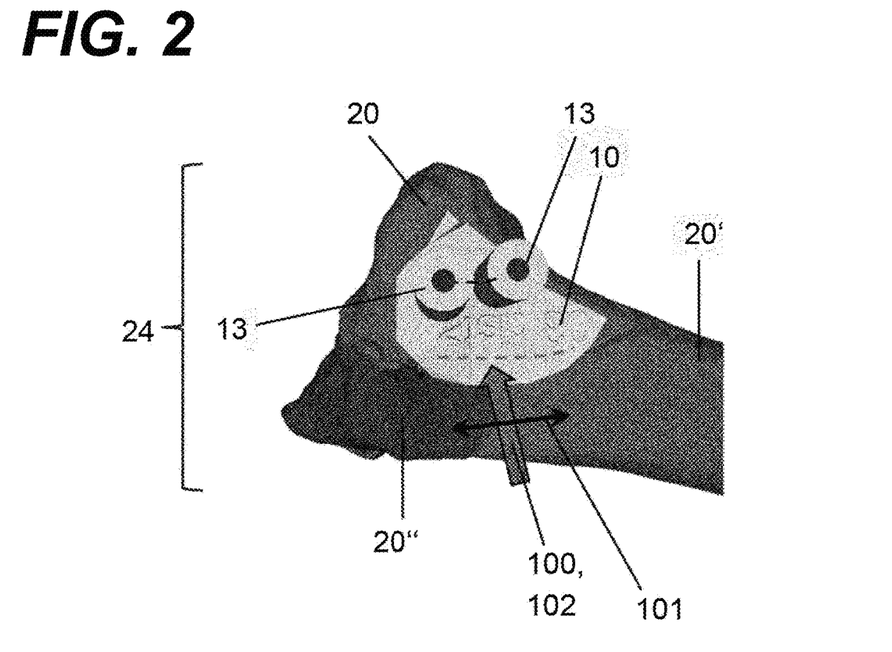
FIG. 2 a three-dimensional view of a fractured bone with the registration instrument.

The second contact surface 12 complements a second surface portion 22 of a fragment 20 of a fractured bone 24 (cf. e.g. FIG. 11 and FIG. 2). The first contact surface 11 is essentially a protruding element on the registration instrument 10 (indicated by the arrows in FIG. 1), wherein the first contact surface 11 is a complementary surface of a first surface portion 21 of the fragment 20 of the fractured bone 24 (cf. e.g. FIG. 11).

Said first surface portion 21 of the fragment 20 is a pathological surface portion, i.e., it comprises an area that was not exposed to the surrounding when the bone 24 was not fractured.

In the present example, the first surface portion 21 is a fracture edge of the fractured bone 24. The edge 23 extends along one of the fragments 20. The fragment 20 also comprises the non-pathological second surface portion 22.

As the fracture edge 23, i.e., the first surface portion 21, has a specific contour and the second surface portion 22 has a specific surface contour as well, the contours of both surface portions 21, 22 of the fragment 20 can serve as landmarks for aligning the registration instrument 10.

Moreover, the surface portions 21, 22 provide a constraint to the registration instrument 10, when the registration instrument 10 is at the correct position on the fragment 20, i.e., when the first surface portion 21 of the fragment 20 and the first contact surface 11 as well as the second surface portion 22 and the second contact surface 12 are in contact and aligned (FIG. 11).

A surgeon can identify this correct position by simultaneously applying a force 100 transversal to the second contact surface 12, i.e., transversal to the fracture edge 23, and along a tangential direction 101 along the fracture edge 23.

If the registration instrument 10 is in the correct position with respect to the fragment 20, the registration instrument 10 should not move with respect to the fragment 20.

The registration instrument 10 when slightly pushed or pressed against the fragment appears like being slightly locked-in to the fragment 20, i.e., it is perfectly fitting.

Once the registration instrument 10 is at the correct position on the fragment 20, a surgical drill can be used to drill pilot holes 30 (cf. e.g. FIG. 5) into the fragment 10 at the positions and orientations defined by the guiding channels 13.

For this purpose, also drill sleeves (not shown) can be inserted in the guiding channels 13.

The position and orientation of the guiding channels 13 on the registration instrument 10 are determined based on a three-dimensional model of the fractured bone 24 and on a three-dimensional reconstruction model 80.

Figure 6:
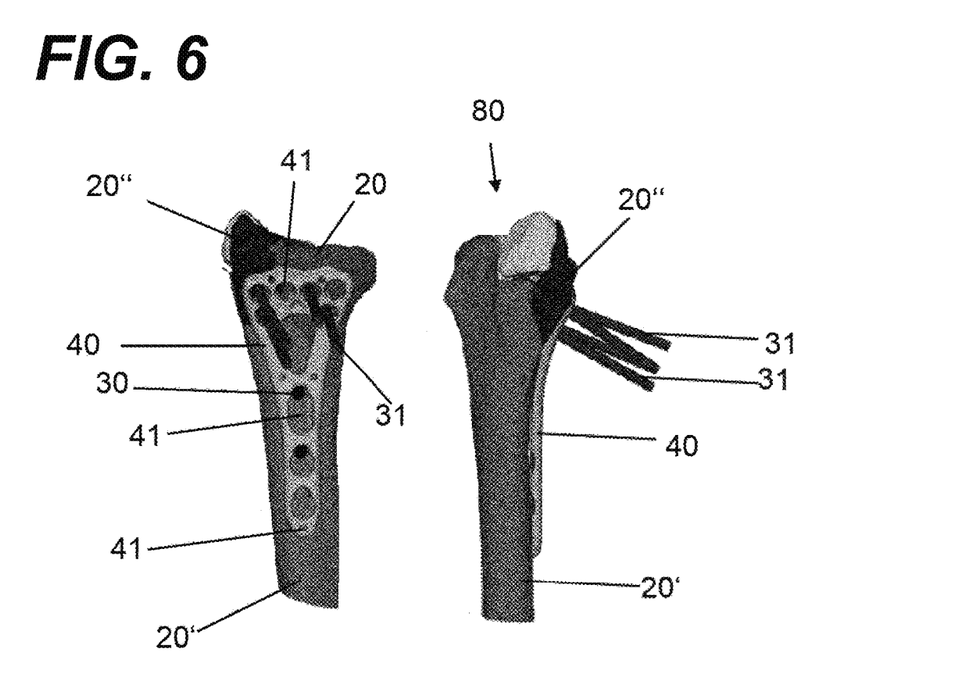
FIG. 6 two three-dimensional views of a broken bone and an osteosynthesis plate.

The reconstruction model 80 provides positions and orientations of all fragments 20, 20', 20" at a predefined healing position, i.e., a position into which the fragments 20, 20', 20" should be brought or repositioned during surgery (cf. e.g. FIG. 6).

The reconstruction model 80 comprises all fragments 20, 20', 20" of the fractured bone 24 in their predefined healing position.

Therefore, the reconstruction model 80 also comprises the pilot holes 30 on the repositioned fragments 20, 20', 20".

Furthermore, the reconstruction model 80 can comprise the surgical pin 31, and surgical screws to be inserted in the pilot holes 30.

Subsequent to drilling the pilot holes 30, a surgical pin in form of a K-wire 31, a screw or a pin can be inserted. The surgical pin 31 can be used as a registration and alignment aid for the fragments 20, 20', 20".

Once the surgical pin, here K-wires, 31 are inserted into the pilot holes 30, the registration instrument 10 can be removed.

For this reason, it is advantageous that the guiding channels 13 are parallel to each other, as otherwise the registration instrument 10 could not be readily removed.

In case the guiding channels 13 cannot be arranged parallel on the registration instrument 10, e.g. due to constrains in accessibility of the fragment 20 during surgery, it is possible to design the guiding channel 13a with an axial slit 15 along the guiding channel wall such that registration instrument 10 can be removed nonetheless through the slit 15. Such a guiding channel 13a is shown e.g. in FIG. 3.

Alternatively, a temporary surgical pin removal, with a subsequent registration instrument 10 removal can be considered. After the registration instrument has been removed, the removed surgical pin(s) can be re-inserted in the corresponding pilot holes.

In FIG. 2 a top view of the registration instrument 10 aligned to the fragment 20 is shown. The bone 24 is broken into three fragments 20, 20', 20", wherein the registration instrument 10 is aligned to and designed for the first fragment 20.

From the top view, the two straight guiding channels 13 can be seen, into which K-wires 31 are inserted after pilot holes 30 have been drilled into the fragment 20 at the corresponding positions.

However, as is illustrated in FIG. 2, the registration instrument 10 has to be aligned with the fragment 20. This is facilitated as follows.

Due to the pathological edge 23 of the fragment 20 (cf. e.g. FIG. 11), onto which the registration instrument 10 is designed to be aligned, a surgeon can recognize, when the registration instrument 10 is in contact with the first surface portion 21, as it is not possible to move the registration instrument 10 further beyond the edge 23 (which is at least a part of the first surface portion 21). Once the first surface portion 21 is aligned with the first contact surface 11 of the registration instrument 10, a recognizable motion constraint along the approach trajectory 102 is provided to the surgeon. In order to identify the correct position of the registration instrument 10 on the fragment 20 also laterally along the edge 23, the registration instrument 10 can by moved transversal 102 to the edge 23 as indicated by the double arrow in FIG. 2 once the first surface portion 21 and the first contact surface 11 are in contact.

When the registration instrument 10 is aligned with the first and second surface portion 21, 22 of the fragment 20, the motion of the registration instrument 10 is constrained, such that a transversal motion 102 is only possible by releasing a contact-maintaining force 100 pointing orthogonally to the transversal force 102.

Figure 4:
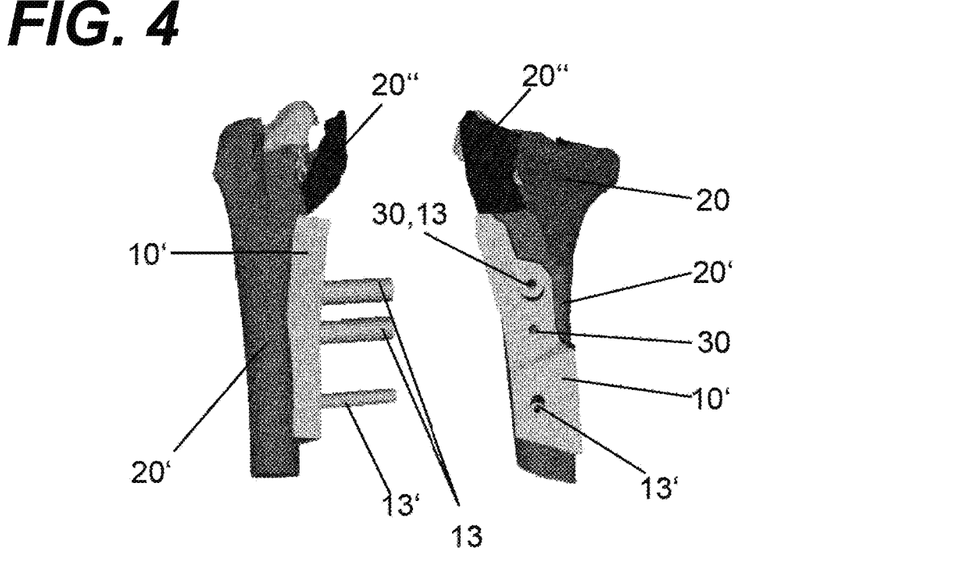
FIG. 4 two three-dimensional views of a broken bone and the registration instrument.
Figure 5:
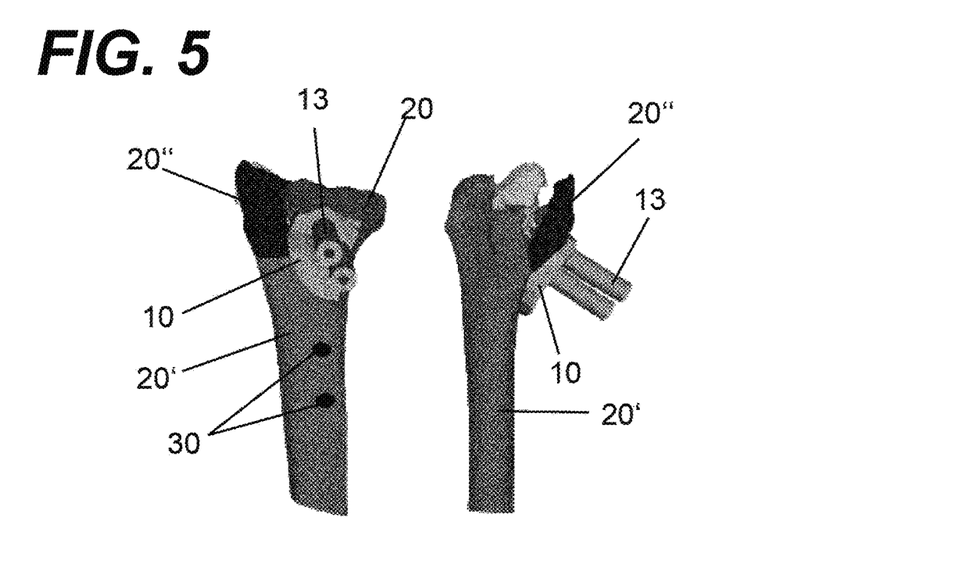
FIG. 5 two three-dimensional views of a broken bone and another registration instrument.

In FIGS. 4, 5, and 6 it is schematically shown how a plurality of registration instruments 10, 10' are used for registering a plurality of bone fragments 20, 20', 20" of a broken joint 24, while FIG. 6 shows the result after repositioning the fragments with the registration instruments 10, 10', and fixing of the fragments with the osteosynthesis plate 40.

In a first step (cf. e.g. different views of the bone 24 in FIG. 4), a first registration instrument 10' designed for a shaft bone fragment 20' is aligned to the correct position as described above with the first and second contact surface. The first registration instrument 10' has three guiding channels 13'.

One guiding channel 13' is for inserting a navigation aid, namely a K-wire, into the fragment 20' at a predefined position and orientation (the most proximal channel 13' in FIG. 4). The other guiding channels 13 are used to drill pilot holes 30 for surgical screws at predefined positions and orientations into the fragment 20'.

Once this has been done, the first registration instrument 10' is removed from the shaft fragment 20' and a second registration instrument 10 is aligned to a joined fragment 20 (FIGS. 1 and 5 in different views). The second registration instrument 10 comprises only two guiding channels 13. In each guiding channel 13, a K-wire is inserted, after pilot-holes have been drilled into the fragment through the guiding channels 13.

Note that the K-wire attached to the shaft fragment is not shown in FIG. 5, but only the pilot holes 30 in the shaft fragment 20'.

The same procedure is performed for a third fragment with a third registration instrument (not shown). Also, in this third fragment, K-wires are inserted as navigation aids.

In a last step, the osteosynthesis plate 40 is arranged on the repositioned fragments 20, 20', 20" and the K-wires 31 are inserted through the corresponding openings 41 in the osteosynthesis plate 40. This is shown in FIG. 6 for different views on the fractured joint 24.

While the opening 41 for the K-wire 31 attached to the shaft fragment 20' is comparably small such that it fits the K-wire 31 tightly, the openings 41 for the K-wires of the second and third fragment 20, 20" are larger. In these openings 41 surgical variable-angle screws will be screwed along a predefined direction into the fragments 20, 20', 20" to fix the osteosynthesis plate 40 to the fragments 20, 20', 20". The fixing of the osteosynthesis plate 40 by the screws is particularly done after aligning the fragments 20, 20', 20" with the osteosynthesis plate 40 into the healing position, particularly by centering the K-wires 31 in corresponding openings of the osteosynthesis plate 40.

In order to center the K-wires 31 with respect to the openings 41 of the osteosynthesis plate 40, an alignment tool 50 can be used.

Figure 7:
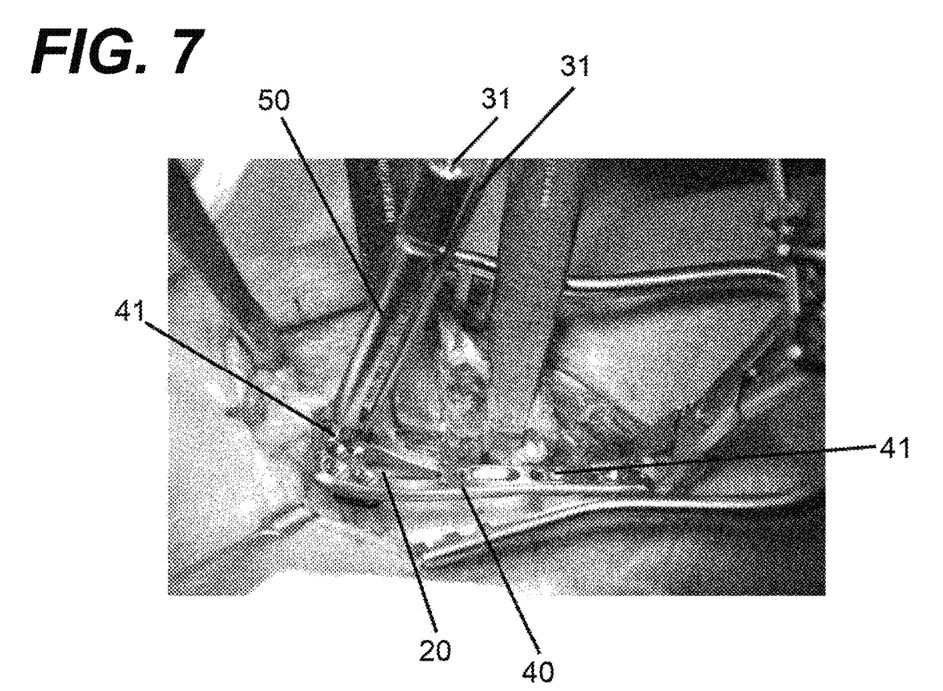
FIG. 7 a picture of an alignment tool attached to an osteosynthesis plate during surgery.

A first variant for aligning the K-wires 31 and thus the fragments 20, 20', 20" to the osteosynthesis plate 40 is provided by the use of an alignment tool 50 that comprises a straight channel for receiving and centering the K-wire 31 (cf. e.g. FIG. 7).

For this purpose, the alignment tool 50 has a hollow thread at one end that can be screwed into the opening of the osteosynthesis plate 40. The opening of the osteosynthesis plate 40 has a matching thread for this purpose. As the channel in the alignment tool is centered with respect to the thread of the alignment tool and tightly fitting the K-wire 31, the K-wire 31 is centered in the opening of the osteosynthesis plate 40, which leads to a perfect position of the osteosynthesis plate 40 with respect to the fragment 20.

The pilot hole 30 diameter and the K-wire 31 diameter are particularly identical, such that reliable centering of the K-wires with the alignment tool 50 can be achieved.

Uniaxial surgical screws can be screwed through free openings 41 of the osteosynthesis plate 40 into perfectly repositioned pilot holes 30 of the fragment 20. The screws fix the osteosynthesis plate 40 rigidly to the fragment 20.

Then, the alignment tool 50 and the K-wires 31 are removed. Surgical screws can be inserted in the now free pilot holes of the K-wires 31.

A second variant (not shown) for aligning the osteosynthesis plate 40 with the fragments 20, 20', 20" makes use of cannulated uniaxial screws.

In this variant, a cannulated screw receives the K-wire in its tightly fitting, centered cannula, while the K-wire extends through a threaded opening of the osteosynthesis plate.

The cannulated screw centers the K-wire, and thus aligns the fragment with respect to the osteosynthesis plate. The cannulated screw is screwed in the thread of the opening and further into the fragment such that the osteosynthesis plate is rigidly attached to the fragment.

A third variant (cf. e.g. FIG. 8) is to provide straight pins 60 that are screwed into the threaded openings of the osteosynthesis plate 40. These pins 60 can be stiffly inserted in the pilot holes and thus provide a defined orientation and positioning of the osteosynthesis plate 40 with respect to the fragment.

Figure 8:
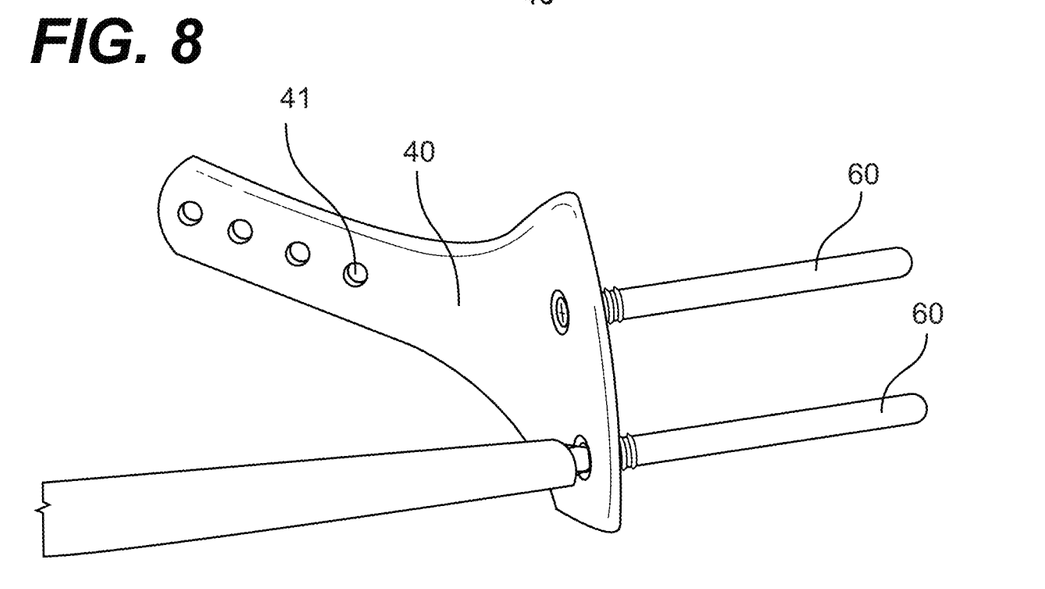
FIG. 8 an osteosynthesis plate with alignment pins attached.

The pins 60 particularly remain in the bone until the fracture is healed.

In the remaining free openings surgical screws for fixing the osteosynthesis plate 40 to the fragment can be screwed.

In yet a fourth variant (cf. e.g. FIG. 9A+9B) a post-registration instrument 70 is applied that has centering channels 71 for centering the K-wires 31 inserted in the repositioned fragments 20.

Figure 9A:
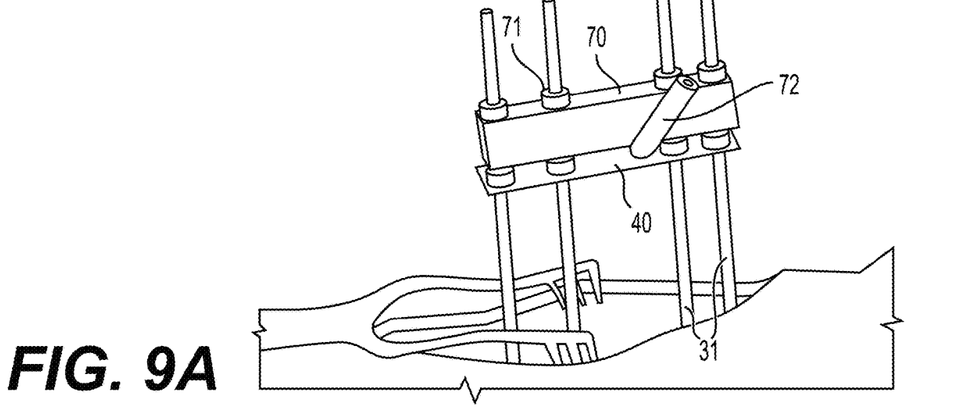
FIG. 9A+B a post-registration instrument applied during surgery.
Figure 9B:
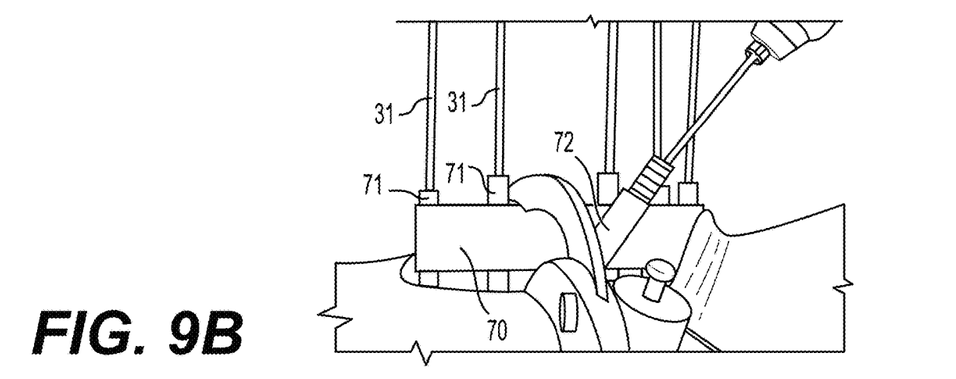

The post-registration instrument 70 is configured to be put on top of the osteosynthesis plate 40 and provide a tight and centered fit for the K-wires 31 with respect to the openings 41 on the osteosynthesis plate 40 and thus a precise alignment of the fragments (FIG. 9A). The osteosynthesis plate 40 can then be fixed to the fragment 20 by use of uniaxial screws inserted through a separate channel 72 (FIG. 9B) or by inserting the screws into free openings 41 of the osteosynthesis plate 40. After fixing the osteosynthesis plate 40, the post-registration 70 instrument is removed. More screws can then be inserted in free openings of the osteosynthesis plate 40 into corresponding pilot holes 30.

Figure 3:
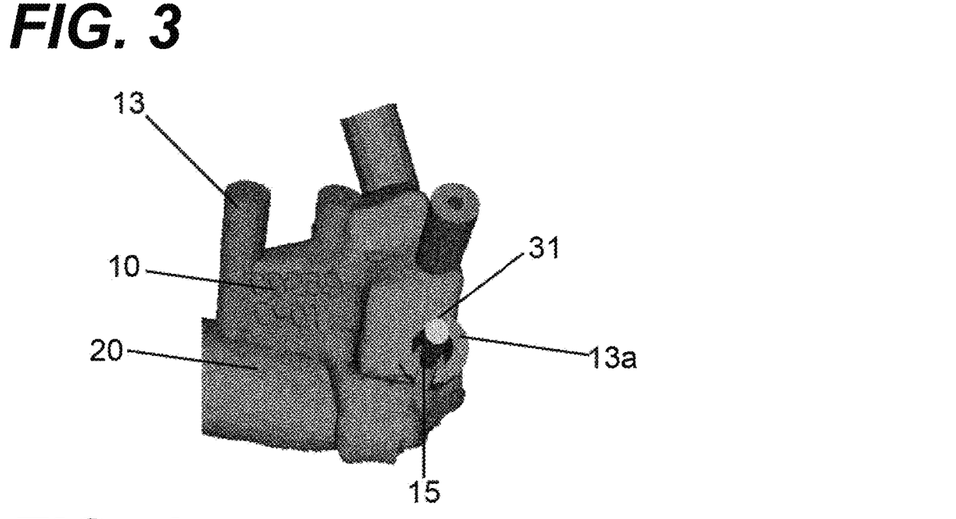
FIG. 3 a three-dimensional view of a registration instrument comprising an open guiding channel.

In FIG. 3, a registration instrument 10 is shown that comprises guiding channel 13a with a slit 15 for removing a K-wire 31 radially through the slit 15 rather than axially.

This is a particularly suitable solution, when the K-wires 31 extend along different orientations through the registration instrument 10, as the registration instrument 10 can be removed despite the non-parallel K-wires.

Figure 10:
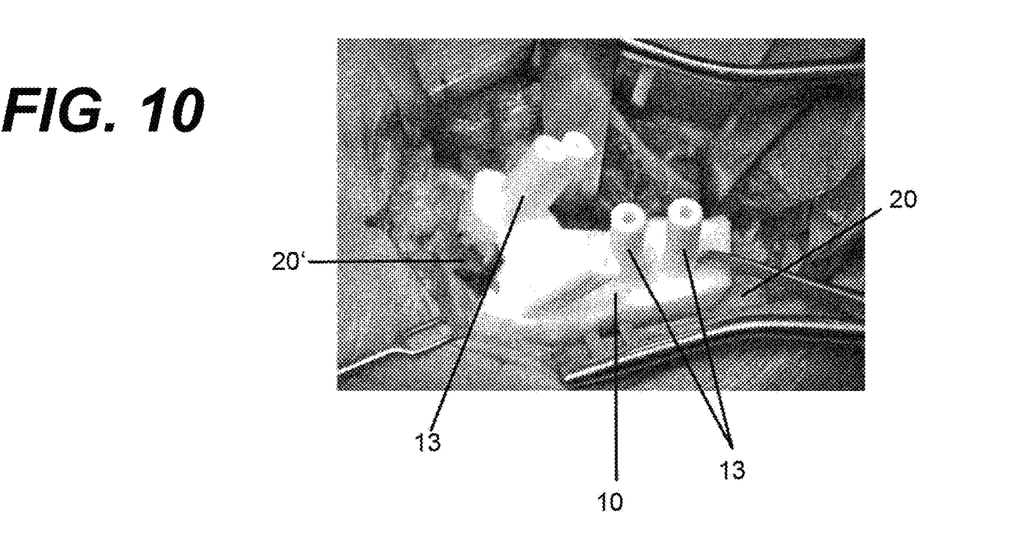
FIG. 10 a single registration instrument for a plurality of fragments applied during surgery.

In FIG. 10 a registration instrument 10 is shown that comprises a plurality of guiding channels 13. The registration instrument 10 extends over a plurality of fragments 20, 20', 20" and the guiding channels 13 are configured to register pilot holes in different fragments.

While the registration instrument 10 is aligned with one fragment 20 as described above, this embodiment allows for a quick and accurate registering of pilot holes on other fragments, particularly when the fragments are not completely separated from each other, and partially immobile. The guiding channels 13 are particularly pairwise parallel, wherein for each fragment parallel guiding channel provide pilot holes along the same orientation.

REFERENCES

[1] Schweizer, A., Mauler, F., Vlachopoulos, L., Nagy, L., & Fürnstahl, P. "Computer-assisted 3-dimensional reconstructions of scaphoid fractures and nonunions with and without the use of patient-specific guides: early clinical outcomes and postoperative assessments of reconstruction accuracy". The Journal of Hand Surgery, (2016) 41(1), 59-69.

[2] Vlachopoulos, L., Schweizer, A., Meyer, D.C., Gerber, C., Fürnstahl, P. "Three-dimensional corrective osteotomies of complex malunited humeral fractures using patient-specific guides"; Journal of Shoulder and Elbow Surgery (2016) Dec. 25(12): 2040-2047; doi: 10.1016/j.jse.2016.04.038.*

The invention claimed is:

1. A surgical tool system for osteosynthesis of a fractured bone comprising bone fragments, the surgical tool system comprising at least one registration instrument for registering a fractured bone fragment in a predefined healing position and at least one post-registration instrument, the registration instrument comprising:

a first contact surface and a second contact surface, wherein the first and the second contact surfaces meet at along an edge, wherein the first contact surface is an inverse surface of a first surface portion of a fragment of the fractured bone and the second contact surface is an inverse surface of a second surface portion of the fragment; and at least one guiding channel configured to provide guidance to a surgical tool for drilling pilot holes at predefined orientations and positions into a bone fragment;

wherein the surgical tool system further comprises an osteosynthesis plate for rigidly fixing the fragments together in a predefined healing position that corresponds to a position in which the bone should be reconstructed from the fragments, the osteosynthesis plate comprising a plurality of openings for receiving surgical tools, wherein the openings correspond to the positions and orientations of the pilot holes in the fragments when the fragments are repositioned in the predefined healing position;

wherein the post-registration instrument is configured to align the fragments of the fractured bone with the osteosynthesis plate, while the osteosynthesis plate is arranged at the fragments, wherein the post-registration instrument is configured to align the positions of the pilot holes with centers of the openings of the osteosynthesis plate; and wherein the post-registration instrument comprises centering channels for receiving surgical pins configured to be attached to different fragments of the fractured bone, wherein the centering channels are configured to center the surgical pins with respect to the openings of the osteosynthesis plate.

2. The system according to claim 1, wherein the at least one guiding channel comprises a slit axially extending along the guiding channel such that a surgical pin inserted in the guiding channel can be removed along a radial direction of the guiding channel through the slit.

3. The system according to claim 1, wherein the at least one registration instrument comprises a plurality of registration instruments.

4. The system according to claim 1, wherein at least a fraction of the openings of the osteosynthesis plate comprises a thread with a thread axis.

5. The system according to claim 4, wherein the system comprises a straight and rigid pin that can be screwed in the thread of an opening of the osteosynthesis plate, wherein the straight pin, when screwed in the opening, extends along the thread axis of the opening and wherein the straight pin fits in a pilot hole, such that the osteosynthesis plate assumes a predefined orientation and position with respect to the fragments.

6. The system according to claim 4, wherein the system comprises a cannulated screw that can be screwed in the thread of an opening of the osteosynthesis plate, wherein the cannulated screw is configured to center a surgical pin in its cannula with respect to the opening and wherein the cannulated screw is configured to be screwed further into the corresponding pilot hole and rigidly connects the osteosynthesis plate with the fragment, wherein the cannulated screw is a uniaxial screw, a compression screw or a variable angle screw.

7. A method for designing the surgical tool system for osteosynthesis of a fractured bone according to claim 1 including a method for designing a patient-specific registration instrument comprising the steps of:
   acquiring a three-dimensional model of a fractured bone, wherein the fractured bone is broken in a plurality of fragments that are at least partially disjoint;
   determining a first surface portion of one fragment, wherein the first surface portion comprises a pathological surface of the fragment;
   determining a second surface portion of the fragment, wherein the second surface portion comprises a non-pathological bone surface; and
   manufacturing a registration instrument comprising a first contact surface and a second contact surface, wherein the first contact surface is an inverse surface of the first surface portion of the fragment and wherein the second contact surface is an inverse surface of the second surface portion of the fragment, wherein the first and second surface portions of the fragment and the first and second contact surfaces each comprise a non-planar surface such that the registration instrument fits to the fragment only if the first and second contact surfaces are aligned with the first and second surface portions of the fragment.

8. The method according to claim 7, wherein the first and the second surface portions of the fragment are determined such that they are accessible to the registration instrument during surgery, and wherein the first and the second surface portions of the fragment constrain further motion of the registration instrument when the registration instrument is in contact with and aligned to the first and the second surface portions with its corresponding first and second contact surfaces.

9. The method according to claim 7, wherein the first and the second surface portions of the fragment are determined such that they are accessible to the registration instrument during surgery along a predefined trajectory, and wherein the first and the second surface portions of the fragment constrain further motion of the registration instrument beyond the predefined trajectory and along a motion transverse to the predefined trajectory of the registration instrument when the registration instrument is in contact with and aligned to the first and the second surface portions with its corresponding first and second contact surfaces.

10. The method according to claim 7, wherein the registration instrument further comprises a plurality of guiding channels at predefined positions and orientations in the registration instrument are determined and manufactured into the registration instrument, wherein each guiding channel is configured to provide guidance to a surgical tool particularly for drilling a pilot hole at a predefined orientation and position into the bone.

11. The method according to claim 7, wherein a three-dimensional reconstruction model is generated that represents the surface of a non-fractured bone configuration of the fractured bone, wherein the three-dimensional reconstruction model comprises the repositioned fragments.

12. The method according to claim 11, wherein the reconstruction model comprises the repositioned fragments and correspondingly repositioned orientations and positions of pilot holes in the fragments,
   wherein the method further comprises designing an osteosynthesis plate, the osteosynthesis plate comprising a plurality of openings that correspond to the repositioned positions and orientations of the pilot holes.

13. The method according to claim 7, wherein a separate registration instrument is designed for each fragment.

* * * * *